United States Patent [19]
Kouri

[11] Patent Number: 6,086,866
[45] Date of Patent: Jul. 11, 2000

[54] USE OF PLATELET-DERIVED GROWTH FACTOR TO IMPROVE COLLATERAL CIRCULATION

[76] Inventor: Roger Khalil Kouri, No. 2 Kingsbury, St. Louis, Mo. 63112

[21] Appl. No.: 08/875,357
[22] PCT Filed: Apr. 29, 1994
[86] PCT No.: PCT/US94/04762
§ 371 Date: Nov. 27, 1996
§ 102(e) Date: Nov. 27, 1996
[87] PCT Pub. No.: WO94/25056
PCT Pub. Date: Nov. 10, 1994

Related U.S. Application Data

[63] Continuation-in-part of application No. 08/055,062, Apr. 29, 1994, abandoned.
[51] Int. Cl.$^7$ ............................................. A61K 38/18
[52] U.S. Cl. ............................................. 424/85.1; 514/2
[58] Field of Search ................................ 424/85.1; 514/2

[56] References Cited

U.S. PATENT DOCUMENTS 5,194,596  3/1993  Tischer et al. ..................... 530/399
5,312,333  5/1994  Churinetz et al. ..................... 604/57

OTHER PUBLICATIONS

Greehalgh et al. Amer. J. Pathol. 136:1235–1246, Jun. 1990.
Bowie et al. Science 247:1306–1310, 1990.
Wells. Biochemistry 29:8509–8517, 1990.
Ngo et al., The Protein Folding Problem and Tertiary Structure Prediction, Merz et al., eds., Birkhauser, Boston, pp. 492–495, 1994.
Schulz et al., Principles of Protein Structure, Springer–Verlag, NY, pp. 14–16, 1979.
Benjamin et al. Development 125:1591–1598, 1998.

*Primary Examiner*—Elizabeth Kemmerer
*Attorney, Agent, or Firm*—Howell & Haferkamp, L.C.

[57] ABSTRACT

The present invention provides a non-invasive method for improving collateral circulation to tissue at risk of ischemia or ischemic necrosis. Improved collateral circulation is obtained by applying a growth factor from the PDGF family to the area at or around an occluded blood vessel causing compromised direct circulation to the affected tissue. The present invention further provides a method for anastomosing one or more divided blood vessels using a growth factor from the PDGF family. Preferably, the growth factor is administered locally to the end(s) of the divided blood vessel(s) at or around the area where a single divided blood vessel is attached to tissue of an organ at risk of ischemia.

4 Claims, 15 Drawing Sheets

```
                                            10                    30                         50
                                  CTAGAAGGAGGAATAACATATGTCTCTGGGTTCGTTAACCATTGCGGAACCGGCTATGAT      60
                              1   ----+----|----+----|----+----|----+----|----+----|----+----|
                                  TTCCTCCTTATTGTATACAGAGACCCAAGCAATTGGTAACGCCTTGGCCGATACTA
                                                  MetSerLeuGlySerLeuThrIleAlaGluProAlaMetIl
                                                  1

70                    90                        110
                                  TGCCGAGTGCAAGACACGAACCGAGGTGTTCGAGATCTCCCGGCCCTCATCGACCGCAC     120
                             61   ----+----|----+----|----+----|----+----|----+----|----+----|
                                  ACGGCTCACGTTCTGTGCTTGGCTCCACAAGCTCTAGAGGGCCGGGAGTAGCTGGCGTG
                                  eAlaGluCysLysThrArgThrGluValPheGluIleSerArgArgLeuIleAspArgTh
                                  14

130                   150                        170
                                  CAATGCCAACTTCCTGGTGTGCCGCCCTGCCTGGAGGTGCAGGCTGCTCCGGCTGTTG     180
                            121   ----+----|----+----|----+----|----+----|----+----|----+----|
                                  GTTACGGTTGAAGGACCACACGGGCGGGACGGACCTCCACGTCCGACGAGGCCGACAAC
                                  rAsnAlaAsnPheLeuValTrpProProCysValGlnValGlnArgCysSerGlyCysCy
                                  34

FIG. IA
```

```
                        190         210       230              240
                         .           .          .
      CAACAACCGCAAGTGCAGTGCCGGCCCACCCAGGTGCAGCTGCCGGGCCAGTCCAGGTGAG
181   ------------+---------+---------+---------+---------+---------+
      GTTGTTGGCGTTCACGTCACGGCCGGGTGGGTCCACGTCGACGGCCCGGTCAGGTCCACTC
      sAsnAsnArgLysValGlnCysArgProThrGlnValGlnLeuArgProValGlnValAr
                                    54

250         270       290              300
                         .           .          .
      AAAGATCGAGATTGTGCGGAAGAAGCCAATCTTTAAGAAGGCCACGGTGACGCTGGAGGA
241   ------------+---------+---------+---------+---------+---------+
      TTTCTAGCTCTAACACGCCTTCTTCGGTTAGAAATTCTTCCGGTGCCACTGCGACCTCCT
      gLysIleGluIleValArgLysLysProIlePheLysLysAlaThrValThrLeuGluAs
                                    74

310         330       350              360
                         .           .          .
      CCACCTGGACATGCAAGTGTGAGACAGTGGCCAGTGCACGGCCTGTGACCCGAAGCCCGGG
301   ------------+---------+---------+---------+---------+---------+
      GGTGGACCTGTACGTTCACACTCTGTCACCGGTCACGTGCCGGACACTGGGCTTCGGGCCC
      pHisLeuAspMetGlnValCysLysGlnTrpValAlaAlaAlaArgProValThrArgSerProGl
                                    94

370         380
                         .           .
      GGGTTCCCAGGAGCAGGCGATAAG
361   ------------+---------+---
      CCCAAGGGTCCTCGTCGCTATTCTTAA
      yGlySerGlnGluGlnGlnArg
                         119
```

FIG. 1B

SEQUENCE LISTING (1) GENERAL INFORMATION:

(iii) NUMBER OF SEQUENCES:  5

(2) INFORMATION FOR SEQ ID NO:1:

(i) SEQUENCE CHARACTERISTICS:
      (A) LENGTH:   34 bases
      (B) TYPE:    nucleic acid
      (C) STRANDEDNESS:   single
      (D) TOPOLOGY:  linear (ii) MOLECULE TYPE:  other nucleic acid (xi) SEQUENCE DESCRIPTION: SEQ ID NO:1:

GGTCACAGGC CGTGCAGCTG CCACTGTCTC ACAC 34

(2) INFORMATION FOR SEQ ID NO:2:

(i) SEQUENCE CHARACTERISTICS:
        (A) LENGTH: 98 bases
        (B) TYPE:  nucleic acid
        (C) STRANDEDNESS:  double
        (D) TOPOLOGY:  linear (ii) MOLECULE TYPE:  other nucleic acid (xi) SEQUENCE DESCRIPTION: SEQ ID NO:2:

AGCTTCTAGA AGGAGGAATA ACATATGTCT CTGGGTTCGT 40

TAACCATTGC GGAACCGGCT ATGATTGCCG AGTGCAAGAC 80

ACGAACCGAG GTGTTCGA 98

(2) INFORMATION FOR SEQ ID NO:3:

(i) SEQUENCE CHARACTERISTICS:
        (A) LENGTH: 30 bases
        (B) TYPE:  nucleic acid
        (C) STRANDEDNESS:  double
        (D) TOPOLOGY:  linear (ii) MOLECULE TYPE:  other nucleic acid (xi) SEQUENCE DESCRIPTION: SEQ ID NO:3:

CCCCCCAAGG GTCCTCGTCG CTATTCTTAA 30

(2) INFORMATION FOR SEQ ID NO:4:

(i) SEQUENCE CHARACTERISTICS:
        (A) LENGTH:  55 bases
        (B) TYPE:  nucleic acid
        (C) STRANDEDNESS:  double
        (D) TOPOLOGY:  linear (ii) MOLECULE TYPE:  other nucleic acid (xi) SEQUENCE DESCRIPTION: SEQ ID NO:4:

CGATTTGATT CTAGAAGGAG GAATAACATA TGGTTAACGC 40

GTTGGAATTC GGTAC 55

(2) INFORMATION FOR SEQ ID NO:5:

(i) SEQUENCE CHARACTERISTICS:
        (A) LENGTH: 386 bases
        (B) TYPE:  nucleic acid
        (C) STRANDEDNESS:  double
        (D) TOPOLOGY:  linear (ii) MOLECULE TYPE:  other nucleic acid (xi) SEQUENCE DESCRIPTION: SEQ ID NO:5:

CTAGAAGGAG GAATAACAT ATG TCT CTG GGT TCG TTA ACC 40
                   Met Ser Leu Gly Ser Leu Thr
                    1            5

ATT GCG GAA CCG GCT ATG ATT GCC GAG TGC AAG ACA 76
Ile Ala Glu Pro Ala Met Ile Ala Glu Cys Lys Thr
  10                 15

CGA ACC GAG GTG TTC GAG ATC TCC CGG CGC CTC ATC 112

-continued

```
Arg Thr Glu Val Phe Glu Ile Ser Arg Arg Leu Ile
20              25                  30

GAC CGC ACC AAT GCC AAC TTC CTG GTG TGG CCG CCC              148
Asp Arg Thr Asn Ala Asn Phe Leu Val Trp Pro Pro
            35              40

TGC GTG GAG GTG CAG CGC TGC TCC GGC TGT TGC AAC              184
Cys Val Glu Val Gln Arg Cys Ser Gly Cys Cys Asn
        45              50              55

AAC CGC AAC GTG CAG TGC CGG CCC ACC CAG GTG CAG              220
Asn Arg Asn Val Gln Cys Arg Pro Thr Gln Val Gln
                60              65

CTG CGG CCA GTC CAG GTG AGA AAG ATC GAG ATT GTG              256
Leu Arg Pro Val Gln Val Arg Lys Ile Glu Ile Val
        70              75

CGG AAG AAG CCA ATC TTT AAG AAG GCC ACG GTG ACG              292
Arg Lys Lys Pro Ile Phe Lys Lys Ala Thr Val Thr
80              85              90

CTG GAG GAC CAC CTG GCA TGC AAG TGT GAG ACA GTG              328
Leu Glu Asp His Leu Ala Cys Lys Cys Glu Thr Val
            95              100

GCA GCT GCA CGG CCT GTG ACC CGA AGC CCG GGG GTT              364
Ala Ala Ala Arg Pro Val Thr Arg Ser Pro Gly Gly
        105             110             115

GGT TCC CAG GAG CAG CGA TAAG                                 386
Ser Gln Glu Gln Arg
                120
```

USE OF PLATELET-DERIVED GROWTH FACTOR TO IMPROVE COLLATERAL CIRCULATION

This application is the national stage application of PCT/US94/04762, filed Apr. 29, 1994, and a continuation-in-part of U.S. patent application No. 08/055,062, filed Apr. 29, 1994.

BACKGROUND

Human platelet-derived growth factor ("PDGF") is believed to be the major mitogenic growth factor in serum for connective tissue cells. The mitogenic activity of PDGF has been documented in numerous studies, wherein PDGF has been shown to positively affect mitogenesis in arterial smooth muscle cells, fibroblast cells lines, and glial cells. Deuel et al., *J. Biol. Chem.*, 256(17), 8896–8899 (1981). See also, e.g., Heldin et al., *J. Cell Physiol.*, 105, 235 (1980) (brain glial cells); Raines and Ross, *J. Biol. Chem.*, 257, 5154 (1982) (monkey arterial smooth muscle cells). PDGF is also believed to be a chemoattractant for fibroblasts, smooth muscle cells, monocytes, and granulocytes. Because of its apparent abilities to both induce mitogenesis at the site of connective tissue wounds, and to attract fibroblasts to the site of such wounds, PDGF is thought to have particular potential for therapeutic use in the repair of injured, or traumatized, connective tissues.

Other members of the PDGF family include vascular endothelial cell growth factor ("VEGF", sometimes also referred to as "vascular permeability factor, or "VPF") and placental growth factor ("PLGF"). Tischer et al., *Biochem. Biophys. Res. Comm.*, 165(3), 1198–1206 (1989) and Maglione et al., *Proc. Natl. Acad. Sci. USA*, 88, 9267–9271 (1991), respectively. Both VEGF and PLGF form disulfide bonded dimers from the eight highly conserved cysteine residues that appear in the PDGF homologous region of each monomeric unit of these PDGF family members. Tischer et al. and Maglione et al., ibid. The receptors for VEGF and PLGF are also in the same receptor subfamily as the PDGF receptors. Consequently, these "newer" members of the PDGF family are thought to be potentially useful as therapeutic products in wound repair, although they have not been studied as extensively as PDGF.

Naturally occurring PDGF is a disulfide-bonded dimer having two polypeptide chains, namely the "A" and "B" chains, with the A chain being approximately 60% homologous to the B chain. Naturally occurring PDGF is found in three dimeric forms, namely PDGF-AB heterodimer, PDGF-BB homodimer, or PDGF-AA homodimer. Hannink et al., *Mol. Cell. Biol.*, 6, 1304–1314 (1986). Although PDGF-AB has been identified as the predominate naturally occurring form, it is the PDGF-BB homodimer that has been most widely used in wound healing studies. Each monomeric subunit of the biologically active dimer, irrespective of whether it is an A chain monomer or a B chain monomer, contains eight cysteine residues. Some of these cysteine residues form interchain disulfide bonds which hold the dimer together.

The PDGF-B found in human platelets has been identified as a 109 amino acid cleavage product (PDGF-$B_{109}$) of a 241 amino acid precursor polypeptide Johnsson et al., *EMBO Journal*, 3(5), 921–928 (1984). This 109 amino acid homologous sequence coincides with the 109 amino acid cleavage product of the c-sis encoded PDGF-B precursor protein and is believed by many to be the mature form of PDGF in humans. Homology with the c-sis encoded precursor protein begins at amino acid 82 of the 241 amino acid precursor protein and continues for 109 amino acids. Another form of PDGF-B (PDGF-$B_{119}$), corresponding to the first 119 amino acids of the c-sis encoded PDGF-B precursor protein, has also been identified as a major cleavage product of the c-sis encoded precursor protein when the entire c-sis gene is encoded into a transfected mammalian host. U.S Pat. No. 5,149,792.

The application of PDGF to dermal wounds, including incisional wounds and dermal ulcers, in human and/or animals has been shown to accelerate the rate at which these types of wounds heal. Pierce et al, 167, *J. Exp. Med.*, 974–987 (1988) (incisional wounds in rats); Robson et al., The Lancet, 339, 23–25 (1992) (human dermal ulcers). PDGF has is believed to function in the acceleration of wound healing by stimulating the deposition of a provisional matrix in the wound bed. Pierce et al., *Am. J. Pathology*, 140(6), 1375–1388 (1992). PDGF is also believed to indirectly stimulate supportive angiogenesis in connection with the deposition of this provisional matrix. Pierce et al., ibid. However, this degree of supportive angiogenesis may be insufficient for PDGF alone to significantly accelerate the healing of ischemic wounds. Pierce et al., ibid. More importantly, PDGF has not demonstrated an ability to create collateral circulation in ischemic tissue at risk of necrosis.

Currently, the best method for providing collateral circulation to tissue at risk of ischemic necrosis is surgical anastomosis, or bypass surgery. Although advances in endoscopic technology have made it possible to perform some cardiac surgical procedures through a thoracoscope (Mack et al.,*Ann. Thorac. Surg.*, 56, 739–740 (1993); Hazelrigg et al., *Ann. Thorac. Surg.*, 56, 792–795 (1993); Frumin et al., *PACE*, 16, 257–260 (1993)), it is not possible to perform coronary artery bypass grafting through a thoracoscope without cardiopulmonary bypass unless and until coronary artery anastomoses can be performed reliably and safely on a beating heart.

Thus, there are no established noninvasive procedures for creating collateral circulation in tissue at risk of ischemia. Nevertheless, fibroblast growth factor (FGF), considered to be the prototypical angiogenic agent, has been suggested in the treatment of ischemic heart disease and to alleviate conditions caused by myocardial infarction. U.S. Pat. Nos. 4,278,347 and 4,296,100, respectively. Yanagisawa et al. *Science*, 257, 1401–1403 (1992) have also injected basic FGF into the proximal coronary circulation and demonstrated a reduction in the size of myocardial infarction upon coronary occlusion. This approach, however, relies upon good blood flow in the very same coronary circulation that has already been compromised by the atherosclerotic disease process. Unger et al., *Am. J. Physiol.*, 264, H1567–H1574 (1993), reported that implanting the internal mammary vessels into the left ventricular myocardium, with infusion of acidic FGF into the distal ends of the implanted vessels, resulted in no beneficial effect beyond that which was achieved with heparin infusion alone.

It is an object of the present invention to provide a noninvasive method for improving collateral circulation in tissue at risk of ischemia-or ischemic necrosis.

It is a further object of the present invention to provide a noninvasive method to effect the anastomosis of blood vessels.

It is a still further object of the present invention to provide a nonsurgical method for conducting bypass grafting.

SUMMARY OF THE INVENTION

The present invention provides a noninvasive method for improving collateral circulation in or around the area of an occluded blood vessel, or a blood vessel at risk of occlusion, through the application of a growth factor from the PDGF family. The present invention further provides a method for anastomosing blood vessels using a growth factor from the PDGF family. Anastomosis can involve the reconnection of two divided blood vessels or the connection of a single divided blood vessel to the circulation bed of a tissue at risk of ischemia. The tissue growth factor can be administered by local administration to the affected ischemic tissue area or by systemic infusion of growth factor. In the case where anastomosis of one or more blood vessels is desired, the growth factor can be administered directly to the blood vessels desired to be anastomosed or to the area at or around the site where a divided blood vessel is attached to tissue at risk of ischemia.

BRIEF DESCRIPTION OF THE DRAWINGS

FIG. 1A shows nucleotides 1–180 of a nucleic acid coding sequence for PDGF-$B_{119}$ (bases 1–180 of SEQ ID NO:5), along with the corresponding amino acid sequence.

FIG. 1B shows nucleotides 181–386 of a nucleic acid coding sequence for PDGF-$B_{119}$ (bases 181–386 of SEQ ID NO:5), along with the corresponding amino acid sequence.

DETAILED DESCRIPTION OF THE INVENTION

Figure 2:
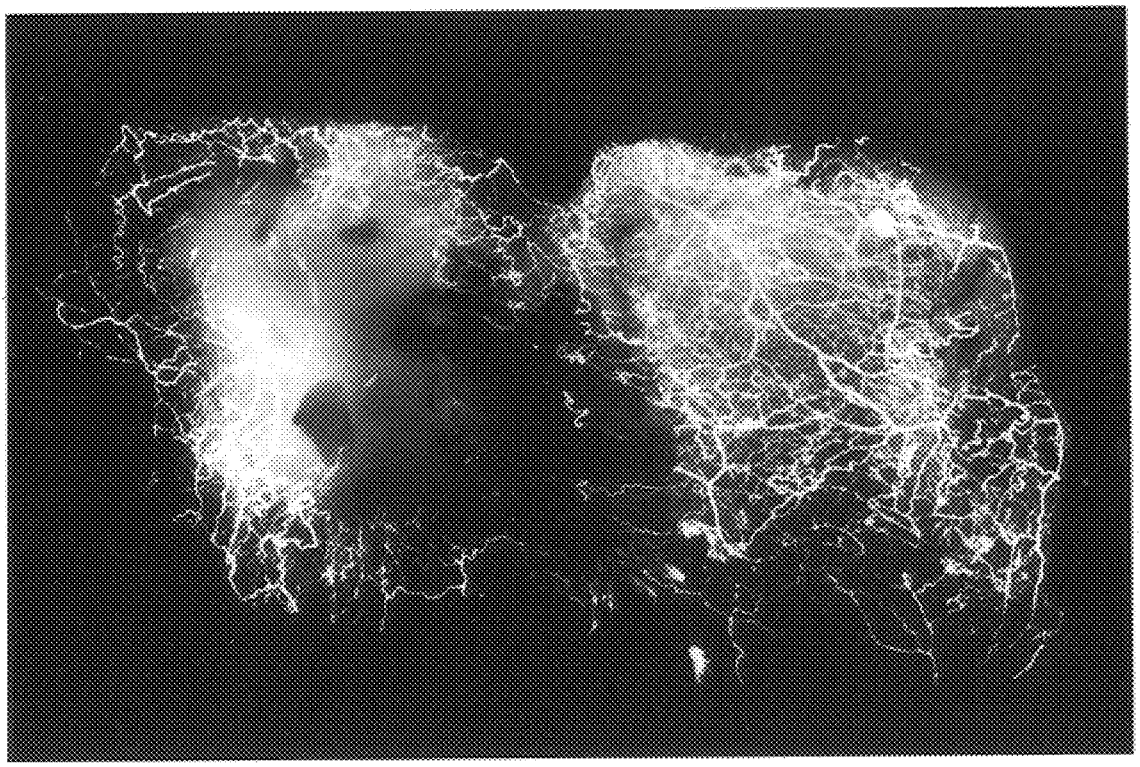
FIG. 2 shows an angiogram of a representative flap taken from a rat in the day-3 group following prophylactic administration of PDGF, as set forth in Example 5.

The present invention provides a method for improving collateral circulation and/or anastomosing blood vessels through the application of a growth factor from the PDGF family.

In order to aid in the understanding of the present invention, the following terms, as used herein, have the definitions designated below.

The term "direct circulation" refers to blood flow resulting from perfusion of blood to a tissue by one of the major direct arteries of the circulatory system to that tissue (e.g., perfusion from the coronary artery to the heart; perfusion from the femoral artery to the leg).

The term "collateral circulation" refers to blood flow that is derived from other than direct circulation.

The term "compromised direct circulation" refers to direct circulation that has been impaired by the occlusion of a blood vessel. Occlusion can occur as the result of any of a number of causes included arterial blockage and division of blood vessels. Ordinarily, compromised direct circulation impaired by at least about 50% begins to place tissue at risk of necrosis.

As used herein "occlusion" of a blood vessel means any degree of restriction of normal blood flow through the occluded blood vessel to its ultimate location(s). Occlusion can occur as the result of stricture of a blood vessel (e.g., arterial blockage; ligation) or from severing (division) of a blood vessel.

The term "improved collateral circulation" refers to collateral circulation that has been increased to a level sufficient to sustain the viability of the affected ischemic tissue.

The term "anastomose" or "anastomosis" refers to the union of parts or branches of blood vessels so as to allow the blood to flow freely from one vessel to another. Anastomosis can, for example, refer to the union of two divided blood vessels or to the union of a single divided blood vessel with the circulation bed of a tissue.

The term "divided blood vessel" means a blood vessel that has been severed. Blood vessels may be severed either accidentally (e.g., by trauma) or intentionally (e.g., surgical removal of "flap" for reconstructive transplant to another site on the body) of a surgical procedure.

The term "therapeutically effective" amount refers to the amount of PDGF, or other growth factor from the PDGF family, in the absence of other growth factors (i.e., not in the PDGF family), determined to produce improved collateral circulation in a human or animal subject.

As used herein, the term "PDGF" means any combination of PDGF monomers and/or dimers, including analogs thereof, reduced or unreduced, biologically active, or inactive, recombinant or otherwise having substantially the same mitogenic, chemotactic, enzymatic and/or other detectable biological activity as the corresponding naturally-occurring polypeptide. The term "PDGF" is specifically intended to include PDGF analogs having one or more modifications to the number and/or identity of amino acid sequences of naturally occurring PDGF.

As used herein, the term "VEGF" means any combination of VEGF monomers and/or dimers, including analogs thereof, reduced or unreduced, biologically active, or inactive, recombinant or otherwise having substantially the same mitogenic, chemotactic, enzymatic and/or other detectable biological activity as the corresponding naturally occurring polypeptide. The term "VEGF" is specifically intended to include VEGF analogs having one or more modifications to the number and/or identity of amino acid sequences of naturally occurring VEGF.

As used herein, the term "PLGF" means any combination of PLGF monomers and/or dimers, including analogs thereof, reduced or unreduced, biologically active, or inactive, recombinant or otherwise having substantially the same mitogenic, chemotactic, enzymatic and/or other detectable biological activity as the corresponding naturally occurring polypeptide. The term "PLGF" is specifically intended to include PLGF analogs having one or more modifications to the number and/or identity of amino acid sequences of naturally occurring PLGF.

The term "PDGF precursor protein" refers to the entire 241 amino acid c-sis-encoded precursor protein prior to processing of the polypeptide to its shorter, mature forms (e.g., PDGF-$B_{109}$ and PDGF-$B_{119}$).

It has been found according to the present invention that a growth factor from-the PDGF family can be used to improve functional collateral circulation at or around the site of compromised direct circulation. The improved collateral circulation can occur as a result of neovessel formation and/or through the anastomosis of blood vessels. Thus, the present invention provides a method for improving collateral circulation to ischemic tissue resulting from compromised direct circulation of a human or animal subject by administering a therapeutically effective amount of PDGF, or other growth factor from the PDGF family, to the human or animal subject.

There are many medical conditions and disease states that result in compromised direct circulation. For example, myocardial infarction, stroke, and intermittent claudication are examples of compromised direct circulation resulting from atherosclerotic narrowing of the major arterial supply of the heart, brain, and lower extremities, respectively. The conditions of compromised direct circulation naturally induce some limited collateralization of the circulation to augment blood flow to ischemic tissue resulting from compromised direct circulation. However, this normal biological response is often insufficient to create functional collateral circulation in ischemic tissues. Where collateral circulation is not sufficiently improved, the ischemic tissue may die, or necrose, necessitating removal of the necrotic tissue. In the case of myocardial infarction, the heart may cease to function, resulting in death. In the case of compromised direct circulation to extremities, the affected extremity may become gangrenous, requiring amputation.

Thus, in all cases of ischemic tissue at risk of necrosis, it is of utmost importance that collateral circulation to and within the ischemic tissue be improved rapidly. The criticality of rapidly improving collateral circulation to "at risk" tissue is best understood in the context of the fact that brain tissue dies after a mere fifteen minutes of deprivation of its blood supply. Heart tissue may survive up to two hours upon deprivation of its blood supply, but ceases functioning after that point. Other tissues in the body can generally survive no longer than four to six hours before necrosis sets in. Thus, in most cases, it will be preferred to use the method of the present invention to prophylactically improve circulation to ischemic tissue at risk of necrosis, or even to tissue simply at risk of ischemia, similar to the way in which classical surgical procedures of, e.g., heart bypass (to treat heart disease) and leg graft (to treat ischemic disease to the lower extremities) are used. Tissue determined to be at risk, and therefore a candidate for prophylactic treatment by the method of the present invention, will be identified in much the same manner as tissue is currently identified for classical surgical procedures to improve collateral circulation.

In clinical practice, a growth factor from the PDGF family can be administered, e.g., by local administration to the affected ischemic area or by systemic infusion of the growth factor, although local administration is preferred. An example of this type of growth factor application is in the case of "flap" surgery where, in a reconstructive process, tissue is removed from another part of the body and transplanted to the reconstructive site. The administration of a therapeutically effective amount of growth factor at the reconstructive site of the transplant improves collateral circulation, allowing the "flap" tissue to more quickly develop its own collateral blood supply at the reconstructive site and thus dramatically improves the success rate of such types of reconstructive surgery. In the case of reconstructive "flap" surgery, it may be advantageous to apply the growth factor continuously, either by repeated administration of the growth factor, via a sustained release delivery vehicle, or both.

In the case where it is desired to effect anastomosis of divided blood vessels, a growth factor from the PDGF family can be administered at the ends of ligated blood vessels prior to or at the time of anastomosis. For example, when dealing with heart tissue at risk of ischemia or ischemic necrosis, due to imminent occlusion of the arteries responsible for direct circulation (e.g. coronary artery), collateral circulation can be prophylactically improved by endoscopic administration of a therapeutically effective amount of growth factor from the PDGF family to connect purposefully divided blood vessels (e.g., internal mammary artery) from neighboring parts of the body to blood vessels of the heart, thus improving collateral circulation to the heart tissue and obviating the need for the much more invasive classical heart bypass surgery. The ability to endoscopically revascularize a beating heart in this manner, without resorting to a direct surgical coronary artery anastomosis, cardiopulmonary bypass or a median sternotomy wound, significantly reduces the problems currently associated with coronary artery bypass grafting.

It is not necessary, however, for two divided blood vessels to be reconnected in anastomosis procedures. In fact, in the case of by-pass grafting it will often be preferred to perform multiple anastomoses of single divided blood vessels (i.e., by-pass graft vessels) to the circulation bed of tissue of an organ at risk of ischemia. Where it is desired to anastomose a divided graft vessel to the circulation bed of an organ in this manner, the graft vessel is first ligated, cauterized, or otherwise substantially occluded, at the intended point of division and then divided with one of the divided ends simply being attached to the tissue of the affected organ. A therapeutically effective amount of a growth factor from the PDGF family is applied at or near the site of attachment of the graft vessel sometime during the grafting procedure.

Attachment of the graft vessel to the tissue of the affected organ can be performed in any manner known to those skilled in the art. Preferably the attachment is performed by tunneling or burying the graft vessel within the organ tissue. The application of growth factor induces the by-pass graft vessel to connect with the circulation bed of the tissue within which the graft vessel has been placed. The ligature of the graft vessel will typically necrose after attachment, enabling blood to flow from the graft vessel, either though the necrotic tip of the vessel or through vessels which have "sprouted" near the necrotic end, to the vessels of the circulation bed of the affected organ. In this way, no division of blood vessels within the affected organ is required to perform the graft.

The therapeutically effective amount of growth factor from the PDGF family to be administered will vary within a wide range and will depend upon whether the growth factor is being applied for the purpose of increasing collateral circulation in ischemic tissue or for the more acute purpose of anastomosing blood vessels. In the former case, circumstances such as the location and extent of ischemia in affected tissue(s) will play a role in determining the therapeutically effective amount of growth factor. Although in most cases the administration of a single acute application of growth factor will be sufficient to establish the desired level of functional collateral circulation in the affected tissue, it may be necessary in some cases to continue the application of growth factor over a period of several days, or even weeks. The continued treatment may be accomplished by repeated applications of growth factor and/or by a sustained release delivery vehicle. In the case where blood vessels are to be anastomosed, the location and distance between the desired blood vessel sites for anastomosis must be considered as factors in determining the therapeutically effective amount of growth factor. Where anastomosis is desired, it is preferred that the therapeutically effective amount of growth factor be administered in a single application. Where the growth factor is administered in a single application for this purpose, it may be preferred to administer the growth factor via a sustained release delivery vehicle.

Compositions for exogenous application of a growth factor from the PDGF family for increasing collateral circulation are readily ascertained by one of ordinary skill in the art. It will, of course, be appreciated that, like the determination of the therapeutically effective amount, the preferred route of administration of the growth will vary with the condition being treated. While it is possible for the growth factor to be administered as the pure or substantially pure compound, it is preferable to present it as a pharmaceutical formulation or preparation.

The formulations of the present invention, both for veterinary and for human use, comprise a therapeutically effective amount of a growth factor from the PDGF family as above described, together with one or more pharmaceutically acceptable carriers therefore and optionally other therapeutic ingredients. The carrier(s) must be "acceptable" in the sense of being compatible with the other ingredients of the formulation and not deleterious to the recipient thereof. Desirably, the formulation should not include oxidizing or reducing agents and other substances with which peptides are known to be incompatible. The formulations may conveniently be presented in unit dosage form and may be prepared by any of the methods well known in the art. All methods include the step of bringing into association the active ingredient with the carrier which constitutes one or more accessory ingredients. In general the formulations are prepared by uniformly and intimately bringing into association the growth factor with liquid carriers, semi-liquid carriers, or finely divided solid carriers or any combination thereof.

As previously noted, the PDGF family includes PDGF, VEGF and PLGF, all of which are known in the art. The growth factor used to increase collateral circulation and/or to anastomose blood vessels can be any biologically active growth factor from the PDGF family, although it is preferred that the growth factor be PDGF. The PDGF may be a dimeric form of PDGF or a monomeric form of PDGF, as long as the PDGF is biologically active. A preferred form of PDGF is PDGF-BB homodimer. Preferred forms of PDGF-BB homodimer include PDGF-$BB_{109}$ homodimer, PDGF-$BB_{119}$ homodimer, and combinations thereof (e.g., PDGF-$B_{119}B_{109}$ homodimer).

The preferred PDGF can generally be made by any one of a number of methods known to those skilled in the art for the production of recombinant proteins. In many cases, the coding sequences for the PDGF may already be available. It is, of course, also possible to synthesize the desired PDGF coding sequence using a DNA sequenator. The particular method used to generate the coding sequence for the PDGF will ordinarily be dictated by a number of practical considerations including the availability of starting materials.

Once the coding sequence for desired form of PDGF is constructed, it is inserted into a vector, with the resulting vector being used to transfect a suitable host cell using standard techniques known to those skilled in the art. For example, the coding sequences for these subunits can be transfected into a yeast or eucaryotic host cell, and the resulting product recovered from the cell culture, or transfected into an *E. coli* host cell after which the PDGF is folded to form the biologically active protein product.

In the case of a PDGF-BB homodimer, for example, one can first modify the v-sis gene to obtain the human counterpart c-sis, or use C-sis as a starting material. Alternatively, one can either synthesize the PDGF-BB coding sequence, or first cut back the c-sis gene or modified v-sis gene, at an appropriate restriction site near the carboxy terminus, and then rebuild the carboxy terminus of the PDGF precursor protein coding sequence to the desired end position using preferred codons for the particular vector and host cell being employed. The c-sis gene or modified v-sis gene can also be cut back at an appropriate restriction site near the amino terminus, with the amino terminus being built back to the desired starting position, again using preferred codons for the selected vector and host cell systems. In other words, any combination of synthetic methods and in vitro mutagenesis of naturally occurring starting materials can be used to generate PDGF, such as the preferred PDGF-BB homodimer.

The preferred host cell system for production of the fusion dimer of the present invention is a bacterial host cell, preferably *E. coli*. In addition to the particular expression systems herein described, other systems are contemplated by the present invention and include, for example but without limitation, modification of the sites for protease cleavage, and/or use of an alternate leader sequence to increase the level of production of host cells of the fusion dimers of the present invention.

The following examples are provided to aid in the understanding of the present invention, the true scope of which is set forth in the appended claims. Although any form of PDGF is contemplated by the present invention, the PDGF-$BB_{119}$ homodimer was used in the examples which follow. It is understood that modifications can be made in the procedures set forth, without departing from the spirit of the invention.

EXAMPLE 1

Construction of PDGF-$B_{119}$ Coding Sequence

Figure 3:
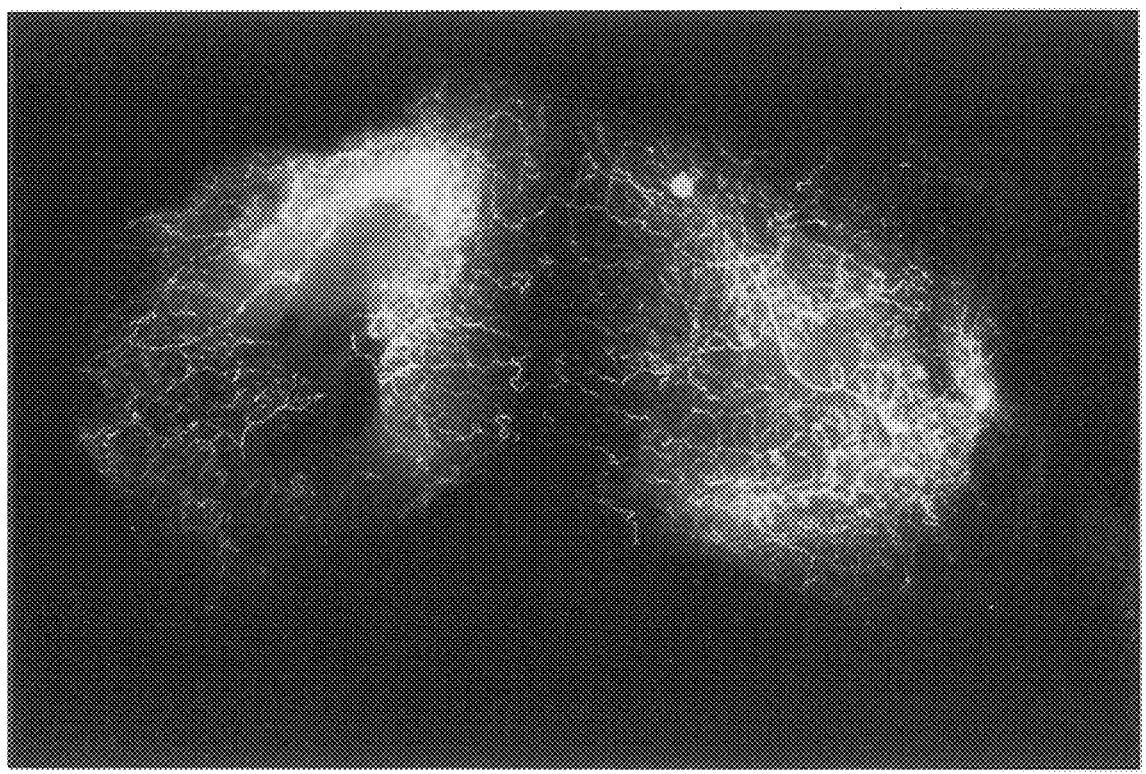
FIG. 3 shows an angiogram of a representative flap taken from a rat in the day-4 group following prophylactic administration of PDGF, as set forth in Example 5.

A PDGF-$B_{119}$ coding sequence, shown in FIG. 3, was constructed using the v-sis gene as a starting material.

A. Conversion of Amino agids 101 and 102

One microgram of the plasmid pC60, a clone of the simian sarcoma virus retroviral genome (Wong-Staal et al., Science, 213, 226–228 (1981)), was digested with restriction endonucleases SAlI and XbaI, with the resulting 1183 base pair fragment then being purified by electrophoretic separation in a low melting temperature agarose gel, in accordance with the procedures described by Maniatis et al., *Molecular Cloning- A Laboratory Manual, Cord Spring Harbor Laboratory* (1982). The purified fragment was then excised from the gel. At the same time, 0.2 μg of M13mp19 DNA was also digested with SalI and XbaI, with the large 7245 base pair band being similarly isolated from a low melting temperature gel. Both excised gel slices were melted at 65° C., and then cooled to 37° C. All of the gel with the 7245 base pair M13mpl9 fragment and one fourth of the gel with the 1183 base pair v-sis fragment were mixed and ligated according to Struhl, *Biotechniques*, 3, 452–453 (1985). The ligated DNA was transformed into *E. coli* K12 strain TG1, and a clear plaque was selected and grown in liquid culture. The presence of the 1183 base pair v-sis fragment in the M13mp19 vector was confirmed by preparation of the RF form of the phage DNA and restriction map analysis. Messing et al., *Nucl. Acids Res.*, 9, 309–321 (1981).

The M13mp19/v-sis phage thus obtained was grown in liquid culture, and the single stranded DNA isolated. Messing et al., ibid. This DNA was used as a template for oligonucleotide-directed in vitro mutagenesis to convert the amino acids at residues 101 and 107 to the corresponding amino acids of PDGF-B. I.e., the ATA codon coding for isoleucine 101 was converted to ACA (coding for threonine), and the GCT codon coding for alanine 107 was converted to CCT (coding for proline).

Ten micrograms of the M13mp19/v-sis single-stranded DNA was annealed with 8 pmol of a phosphorylated oligonucleotide having the sequence (SEQ ID No:1): 5' GGT-CACAGfaCCGTGCAGCTGCCACTfTCTCACAC 3'

This sequence is homologous to nucleotides 4283 to 4316 of the v-sis gene (numbering system of. Devare, et al., *Proc. Natl. Acad. Sci. USA*, 79, 3179–3183 (1982)). The underlined bases of the oligonucleotide denote the changes from the v-sis to the human PDGF-B sequence. DNA synthesis was initiated on the mutant oligonucleotide, with the complete mutant strand being synthesized with the Klenow fragment of *E. coli* DNA polymerase I using thionucleotide triphosphates, followed by ligation with T4 DNA ligase. Any remaining single-stranded template M13mp18/v-sis DNA was removed by filtration on nitrocellulose filters. The non-mutant strand was nicked by incubation with restriction endonuclease III. The nicked non-mutant strand was then repolymerized with the deoxynucleotide triphosphates, using the mutant strand as a template. As a result, both DNA strands in the final product contained the desired mutations. The DNA was transformed into *E. coli* K12 strain TG1. Plaques were selected, grown in liquid culture, and the single-stranded DNA isolated. The DNA was sequenced by the method of Sanger et al., *Proc. Natl. Acad. Sci. USA*, 74, 5463–5467 (1977) to confirm that the desired mutants had been obtained.

B. Conversion of Amino Anids 6 and 7

In the next step, the 5'-end of the mutated v-sis gene was replaced with a synthetic DNA fragment which changed amino acids 6 and 7 from the v-sis to the human PDGF-B forms. This synthetic fragment also provided a translation-initiating ATG codon immediately preceding the codon for serine 1 of human PDGF-B, as well as providing sequences for binding to *E. coli* ribosomes and a restriction site for ligation into the desired *E. coli* expression vector (described below). The synthetic DNA fragment was ligated to the BglII site at nucleotide 4061 of the v-sis gene (numbering system of Devare et al., ibid). Because a BglII site which is present within the M13mp19 vector would complicate and interfere with this step, the mutated v-sis gene was first moved to the commercially available plasmid vector pUC18, which does not contain a BGlII site. The M13mp19/v-sis mutant RF DNA was restricted with SalI and BamH1, and the resulting 1193 base pair fragment isolated by electrophoresis using a low melting temperature agarose gel. This fragment was ligated to the plasmid pUC18 which had also been restricted with SalI and BamH1. The ligated DNA was transformed into the commercially available *E. coli* K12 strain DH5 and transformants were selected by growth in the presence of ampicillin. Colonies were selected, grown in liquid culture, and isolated plasmid DNA analyzed by restriction mapping for the presence of the v-sis insert.

The pUC18/v-sis mutant DNA was restricted with HindIII, which cuts in the polylinker of pUC18 just upstream of the mutated v-sis insert, and with BglII, which cuts within the v-sis DNA at nucleotide 4061 (Numbering system of Devare et al., ibid) corresponding to amino acid number 24 of the mature protein product. The large 3365 base pair fragment resulting from this reaction was isolated by electrophoresis in a low melting temperature agarose gel. This fragment was ligated to a synthetic double-stranded DNA fragment having the following sequence (SEQ ID NO: 2) 5' AGCTTCTAGAAGGAGGAATAACATATGTCTC-TGGGTTCGTTAACCATTGCG-3' AGATCTTCCTCCTTATTGTATACAGAGACCCAAG-CAATTGGTAACGCGAACCGGCTATGAT-TGCCGAGTGCAAGACACGAACCGAGGTGTTCGA 3'-CTTGGCCGATACTAACGGCTCACGTTCTGTGC-TTGGCTCCACAAGCTCTAG 5'

This synthetic DNA fragment contains a HindIII "sticky" end at its upstream (left) end and a BglII "sticky" end at its downstream (right) end. In addition, an XbaI site (TCTAGA) is present within the synthetic DNA just downstream of the HindIII "sticky" end, which allows subsequent restriction with XbaI for ligation into the XbaI site of an expression vector described below. The ligated DNA was transformed into *E. coli* K12 strain DH5, with transformants being selected by growth on ampicillin-containing medium. The plasmid DNAs from resulting colonies were analyzed by restriction mapping for the presence of the synthetic DNA fragment. At this point, the pUC18/v-sis construction contained a mutated v-sis gene, with amino acid number 6, 6, 101, and 107 changed to the human PDGF form, and its 5'-end altered to begin translation with an ATG codon immediately preceding serine 1.

C. Conversion of Amino Acid 114 and Placement of a Stop Codon at Amino Agid 120

In the next step, the codon for amino acid number 114 was changed from ACT to GGT, resulting in the substitution of glycine for threonine in the final protein product. In addition, codon number 120, in which GCC codes for alanine in v-sis, was changed to TAA, a translation termination codon. The resulting protein product of this construction ends with the arginine at residue 119. Both of the changes were accomplished in one step by insertion of a synthetic DNA fragment after a SmaI site located within codon number 112.

The pUC18/v-sis mutant DNA generated above was restricted with SmaI, which cuts at nucleotide 4324 in the v-sis sequence (numbering system of Devare et al., ibid), and with EcoRI, which cuts in the polylinker of pUC18 just downstream of the v-sis insert. A small fragment (510 base pairs) between the SmaI and EcoRI sites, coding for the C-terminal portion of the v-sis protein and a 3'- untranslated sequence, was removed by electrophoresis on a low melting temperature agarose gel. The large fragment (about 3530 base pairs) was ligated to a synthetic DNA fragment having the following sequence (SEQ ID NO: 3): 5' GGGGGGT-TCCCAGGAGCAGCGATAAG 3' 3' CCCCMMGGGTC-CTCGTCGCTATTCTTAA 5'

The GGT codon coding for the new glycine residue at position 114 and the TAA termination codon introduced at position 120 are underlined above. This synthetic DNA fragment contains a blunt end at its upstream (left) and for ligating to the blunt end created by restriction of the v-sis mutant sequence with SmaI, and an EcoRI "sticky" end at its downstream (right) end for ligating to the EcoRI end created by restriction of the pUC18 polylinker with EcoRI. The ligated DNA was transformed into *E. coli* K12 strain DH5, with transformants being selected by growth on ampicillin-containing medium. The plasmid DNAs from resulting colonies were analyzed for the presence of the synthetic DNA fragment by restriction mapping.

EXAMPLE 2

Expression of PDGF-BB$_{119}$ Homodimer in *E. coli*

The completed form of the mutated v-sis gene was removed from pUC18 and ligated into the *E. coli* expression vector pCFM1156. The plasmid pCFM1156PL is prepared from the known plasmid pCFM836. The preparation of plasmid pCFM836 is described in U.S. Pat. No. 4,710,473, the relevant portions of the specification, particularly examples 1 to 7, are hereby incorporated by reference. To prepare pCFM1156 and pCFM836, the two endogenous NdeI restriction sites are cut, the exposed ends are filled with T4 polymerase, and the filled ends are blunt-end ligated.

The resulting plasmid is then digested with ClaI and KpnI and the excised DNA fragment is replaced with a DNA oligonucleotide of the following sequence (SEQ ID NO: 4):
5'→3' ClaI KpnI CGATTTGATTCTAGAAGGAG-
GAATAACATATGGTTAACGCGTTGGAATTCGGTAC
TAAACTAAGATCTTCCTCCTTATTG-
TATACCAATTGCGCAACCTTAAGC 3'→5'

The pCFM1156 vector contains a region for insertion of foreign genes between an upstream XbaI site and one of a number of downstream restriction sites. In this case, the downstream EcoRI site was utilized. The pUC18/v-sis mutant DNA generated above was restricted with XbaI and EcoRI, with the small 383 base pair fragment being isolated by electrophoresis on a low-melting temperature agarose gel. This fragment was ligated to pCFM1156 DNA which had also been restricted with XbaI and EcoRI. The ligated DNA was transformed into *E. coli* strain FM-5 (ATCC NO. 67545), with transformants being selected by growth on kanamycin-containing medium. The plasmid DNAs from resulting colonies were analyzed for the presence of the inserted DNA fragment by restriction mapping.

The final expression plasmid contained an inserted DNA sequence which codes for a protein that begins with an initiating methionine, followed by amino acids 1–119 of the human PDGF-B sequence. The procaryotic *E. coli* host cells removed the N-terminal methionine after synthesis, so that the final protein produced corresponds to amino acids 1–119 of human PDGF-B.

The 119 amino acid PDGF B protein was expressed by growing bacterial cells containing the expression plasmid at 28–30° C. until the desired optical density of the culture was reached, and then shifting the culture to growth at 42° C., and at several time points thereafter.

EXAMPLE 3

Purification and Refolding of PDGF-BB Homodimer

Cells from the *E. coli* fermentation medium of Example 2, containing PDGF-BB$_{119}$, were first suspended in about 3 volumes (wet weight/volume) of water, and then passed three times through a Gaulin homogenizer of 9000 psi. An additional 4 volumes of water were added and the homogenized cells were then centrifuged at 5000×g for 1 hour at 4° C., and the supernatant discarded.

The resulting precipitate (inclusion bodies containing PDGF-BB$_{119}$) was suspended in 6 M guanidine-HCl, 2.5 times cell pellet weight. β-mercaptoethanol was added to a concentration of about 0.14% (v/v), and the suspension mixed for 30 minutes at ambient temperature. This mixture was added to nine volumes of 11 mM Tris-HCl, pH 8.5, and mixing continued for about 20 hours at ambient temperature. The pH was adjusted to about 4 with acetic acid and clarified by filtration. The resulting filtrate was diluted 2-fold with water and then loaded onto an S-Sepharose® column (Pharmacia Biotech, Piscataway, N.J.) equilibrated with 10 mM Tris-HCl, pH 7.7. The loaded column was washed with: (1) 10 Tris-HCl, pH 7.7; then (2) 10 mM Tris·HCl, pH 7.7, 0.3 M sodium chloride; and then (3) 10 mM Tris·HCl, pH 7.5, 0.5 M sodium chloride.

The fractions in the last wash, containing the PDGF-BB$_{119}$, were pooled and applied to a Vydac C4 column equilibrated with 20% ethanol, 10 mM Tris·HCl, pH 7.7. The column was washed with 10 volumes of 20% ethanol, 0.4 M NaCl, 10 mM Tris·Hcl, pH 7.7, and then with 25% ethanol, 0.35 M NaCl, 10 mM Tris·HCl, pH 7.7. Those fractions in the last wash containing PDGF were pooled, acidified with 0.5% (v/v) acetic acid, and then diafiltered, using an Amicon YM® 10 ultrafiltration membrane (Amicon Inc., Danvers, Mass.), with about 6 volumes 0.15 M sodium chloride, 10 mM sodium acetate, pH 4.

EXAMPLE 4

Preparation of a Single Layer Collagen Film

A single layer collagen film containing the purified and refolded PDGF-BB$_{119}$ from Example 3 was prepared according to the procedure set forth in International Publication No. WO/92/22304.

Collagen films were prepared by the solvent casting method from a solution of soluble collagen. The soluble collagen was purchased from Semex Co. (Frazer, Pa.). This collagen is from bovine origin and it contains 99% type I collagen and 1% type III collagen. The molecular weight of the collagen is 300 K dalton and the density is 0.044 gram/cc. The antigenicity of the collagen is minimal since the telopeptide is removed from the collagen.

First, a 4% collagen solution was prepared by dissolving the soluble collagen in 0–5% acetic acid solution at 18–70° C. After the addition of the plasticizer glycerol (about 20% of the dry weight of the collagen), ethanol was added to the solution to facilitate the solvent evaporation process. The amount of alcohol was about 20% of the amount of the solution. The solution was then centrifuged to remove the undissolved material.

A solution containing the purified and refolded PDGF-BB$_{119}$ from Example 3 was added to the 4% soluble collagen solution. The resulting collagen solution, containing PDGF-BB$_{119}$, was cast on a Teflonm surface and dried at room temperature until the weight of the film was constant (for about 1–3 days) to produce collagen films containing 360 µg of the PDGF-BB$_{119}$ homodimer. An additional amount of the 4% collagen solution was prepared in the same manner, but without addition of PDGF, to serve as a negative control in subsequent experiments.

EXAMPLE 5

Induction of Collateral Circulation by PDGF

The rat skin flap model of ischemia-induced angiogenesis of McKee et al., *Plast. Reconstr. Surg.*, 67, 200–204 (1981)

and Tsur et al., *Plast Reconstr. Surg.*, 66, 85–93 (1980) was generally followed to demonstrate the ability of PDGF to improve collateral circulation in ischemic tissue at risk of necrosis, except that the epigastric vessels to the abdominal flap created on the rat were initially kept intact to allow continued direct circulation to the flap following prophylactic application of PDGF. Direct circulation to the flap was later compromised by ligation of the epigastric vascular vessels in a second procedure. The collagen wafers from Example 4 were used for prophylactic administration of PDGF to the surgically created flap prior to occlusion of the blood supply during the second procedure.

Seventy male Fisher rats were anaesthetized with intraperitoneal pentobarbitol (12 to 21 mg) and maintained with supplementary doses. The left groin and abdomen were shaved and depilated, and the animals mounted on a board using standard procedures known in the art. A template was used to mark a 3×6 cm epigastric axial flap with its base over the groin and the medial edge at the midline. The same procedure was repeated with the right groin and abdomen to create two abdominal flaps on each rat. The flaps were then raised bilaterally on the abdominal surface using sharp dissection, dividing all of the blood vessels between the skin flap and the abdomen. At this point, the flaps were still perfused by direct circulation from the epigastric vessels which were kept intact, as described by Petry and Wortham, *Plast. Reconstr. Surg.*, 74, 410–413 (1984). A 2×5 cm PDGF-BB$_{119}$-containing collagen wafer from Example 4 was inserted under one flap on each rat, with a negative control collagen wafer being inserted under the other flap. The flaps were carefully sutured back into place with silk suture following insertion of the collagen wafers. This procedure allowed for prophylactic action by the administered PDGF prior to occlusion of direct blood flow from the epigastric vessels.

A second procedure, designed to compromise direct circulation to the flap at varying points in time following prophylactic administration of PDGF, was carried out 1, 2, 3, 4, 5, 7, or 10 days after the first procedure. Under general anesthesia, the epigastric vascular pedicle in the groin of the rats was exposed on each side and then ligated with silk suture, completely compromising direct circulation to the flap. Sodium fluorescein was injected and the dermatofluorometric index (DFI) was measured 20 minutes later, according to the procedure of Graham et al., *Plast. Reconstr. Surg.*, 71, 826–831 (1983). The area of surviving skin was evaluated 3 days later, using standard planimetric analysis. The aorta was then cannulated and the vasculature flushed with 20 ml. of warm heparinized saline, after which a mixture of lead oxide, saline and gelatin was injected, as described in Rees and Taylor, *Plast. Reconstr. Surg.*, 77, 141–145 (1986). Flap territories were resected and radiographed following overnight refrigeration.

Figure 4:
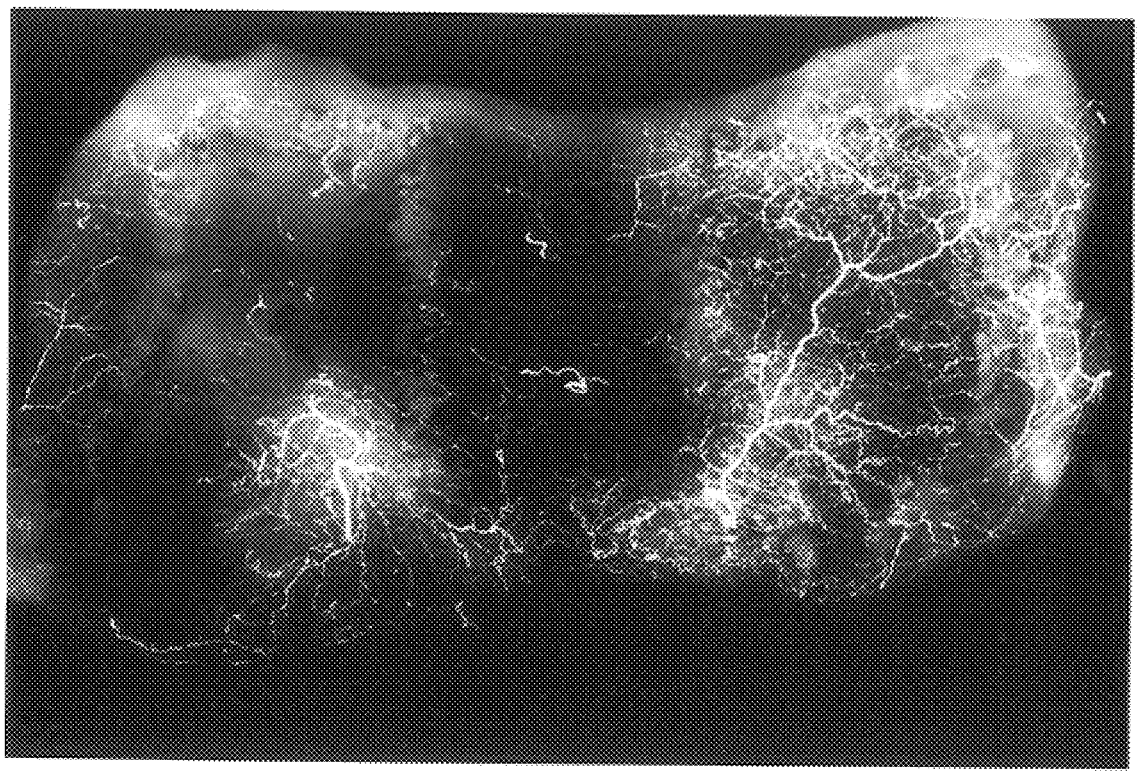
FIG. 4 shows an angiogram of a representative flap taken from a rat in the day-7 group following prophylactic administration of PDGF, as set forth in Example 5.

Samples from rats in the 3-day group demonstrated increased tissue survival of the PDGF-treated flaps. A representative angiogram taken from the 3-day group, shown in FIG. 2, depicts a marked increase in early small blood vessels perfusing the PDGF-treated flap. In the 4-day group, most of the PDGF-treated flaps had developed enough new circulation from the abdomen to achieve complete survival. Unlike the flaps taken from rats in the 3-day group, which showed only an increase in small blood vessels, microangiography of the PDGF-treated flaps taken from rats in the 4-day group revealed large vascular connections from the abdomen to the flap as compared to the control side. A representative angiogram from the 4-day group is shown in FIG. 3. This angiogram demonstrates an abundance of mature functional new vessels on the PDGF-treated flap, and previously divided vessel ends are seen reconnecting across the flap margin. In the 5-day group, the control flaps still had significant necrosis, indicating inadequate perfusion, while the PDGF-treated flaps showed complete survival. A representative angiogram from the day-7 group, shown in FIG. 4, demonstrates the formation of still more new vessels and vascular connections from the margins in the PDGF-treated flaps.

Figure 5:
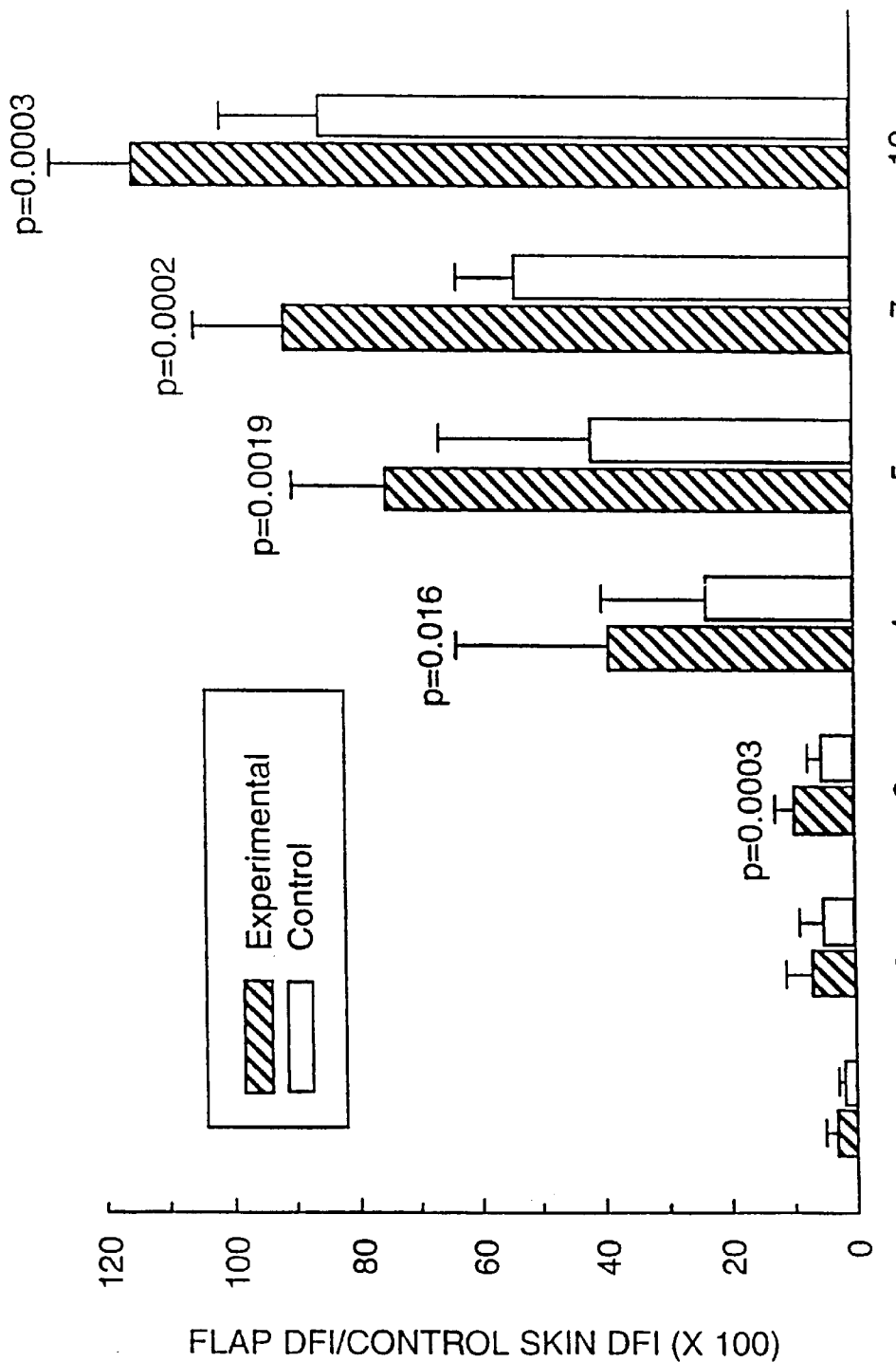
FIG. 5 is a graph showing perfusion by collateral circulation of the flap tissue of the rats in Example 5, as compared to normal skin perfusion.
Figure 6:
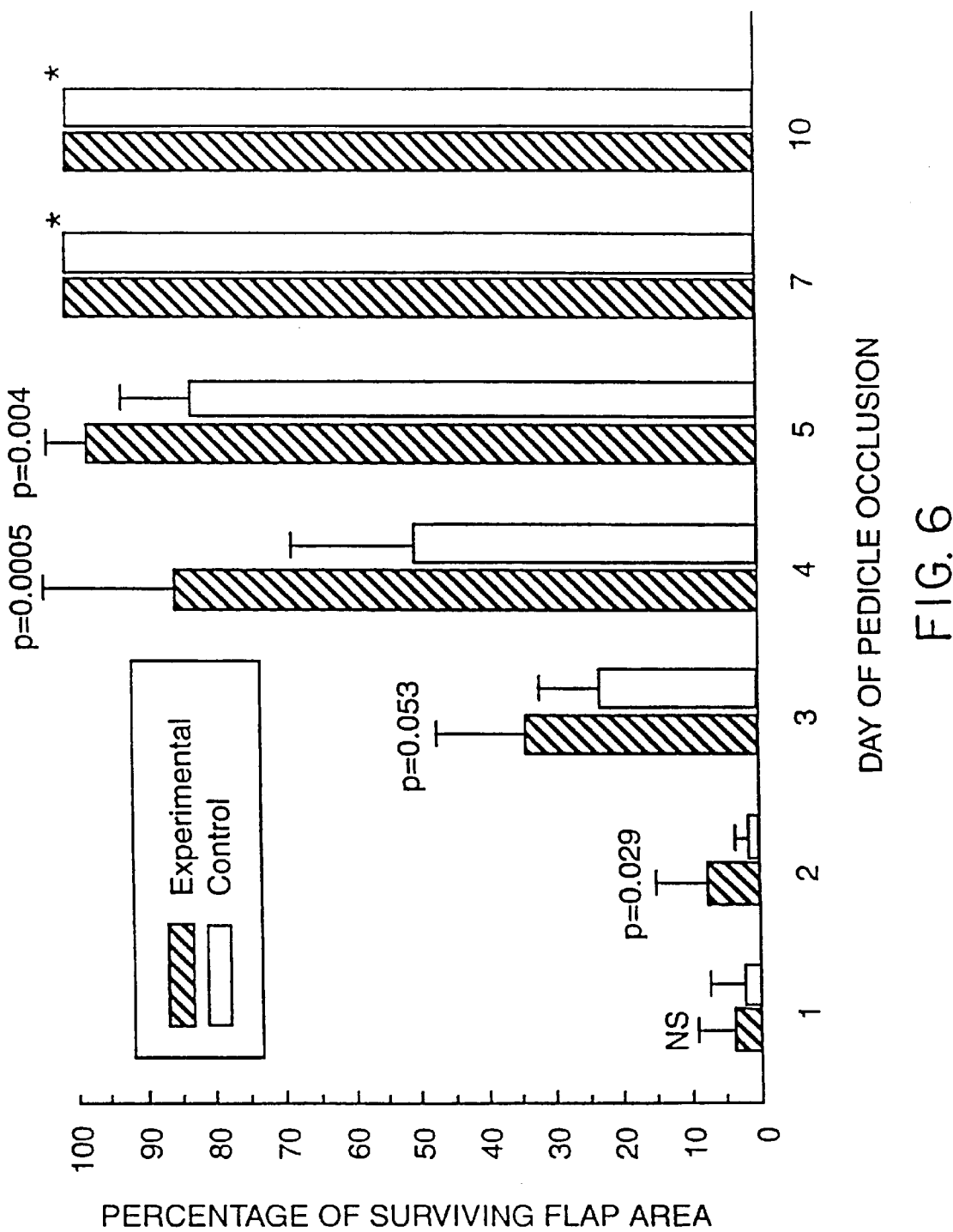
FIG. 6 is a graph showing survival of the flap tissue of the rats in Example 5.

The results of this study are summarized in the graphs displayed in FIGS. 5 and 6. The graph in FIG. 5 shows perfusion of the flap tissue by PDGF-induced collateral circulation relative to normal skin perfusion. By day 5, the PDGF-treated flap had developed almost twice the control amount of perfusion. At day 10, prophylactic treatment of the skin flap tissue with PDGF had caused the tissue to acquire more than normal blood flow (115%), while the untreated control side had only 84.5% of normal blood flow. The flap survival graph in FIG. 6 demonstrates that, at four days, PDGF treatment allowed 85% of the flap to survive, while control flaps had only 49% survival.

EXAMPLE 6

Neovascularization Using PDGF

Figure 7A:
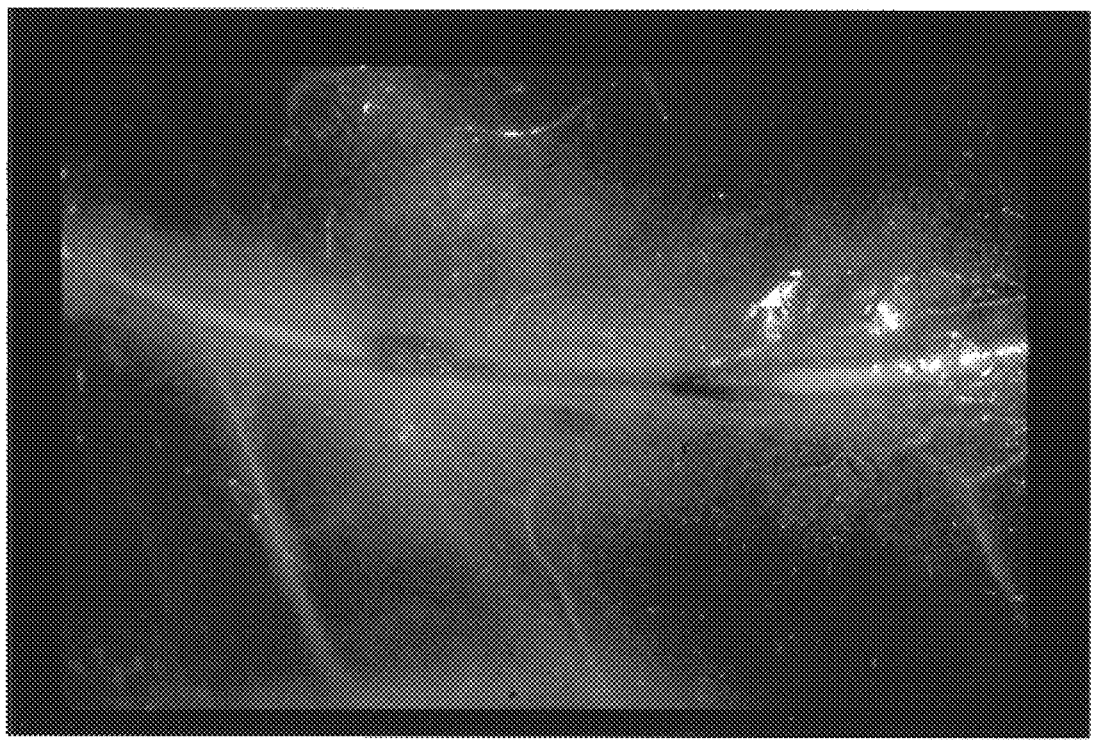
FIG. 7A shows the control vessel from Example 6 in situ after injection with contrast solution.

To examine the ability of PDGF-BB to induce the regeneration of a single large caliber vessel between two vessel ends in 30 retired male Lewis rats, a segment of the superficial femoral artery was cauterized and resected to create a 3–4 mm gap. 200 $\mu$l of either PDGF-BB from Example 3 or an inactive mutant variant of PDGF-BB were injected into the tissue between the two separated ends of the vessel, with each animal serving as his own control. Reconstitution of vascular continuity was evaluated at 2 and 3 weeks by latex injection, direct observation, microangiography (Rees and Taylor, *Plast. Reconstr. Surg.*, 77, 141–145 (1986)), corrosion casts and serial histologic sectioning. After 2 weeks, 33% (4 of 12) of the vessels had re-established continuity in the active PDGF-BB-treated group, while none of the vessels in the control group had regenerated (p<0.05). After 3 weeks, 100% (18 of 18) arteries in the PDGF-BB group had regenerated and re-established patent vascular conduits, while none of the vessels in the control group had reconnected (p<0.0001), as shown in FIG. 7A.

Figure 7B:
FIG. 7B shows the PDGF-B-treated vessel from Example 6 in situ after injection with contrast solution.

On histological evaluation, the regenerated artery was seen with a complete endothelial layer surrounded by smooth muscle tissue. The vessel diameter was comparable in size to the original femoral artery, implicating a response of functional vessel regeneration. The new arterial segment appeared to "sprout" off as a branch vessel close to the thrombosed end of the severed vessel and bridged the gap in a manner similar to a surgical vein graft bypass, as shown in FIG. 7B.

EXAMPLE 7

Cardiac Revascularization using PDGF

This example demonstrates cardiac revascularization on a beating heart without resorting to a surgical anastomosis or cardiopulmonary bypass, combining the angiogenic effect of PDGF-BB with the implantation into the myocardium of an extra-cardiac vessel.

New Zealand white rabbits (3.5–4 kg) were anesthetized with an intramuscular injection of ketamine (15 mg/kg) and xylazine (5 mg/kg). The rabbits were intubated orally, and mechanically ventilated with 100% oxygen. A precordial electrocardiogram (ECG) was recorded throughout each surgical procedure. The NIH "Guide for the Care and Use of Laboratory Animals" (NIH Publication No. 86-23, revised 1985) was followed throughout the study.

Figure 8:
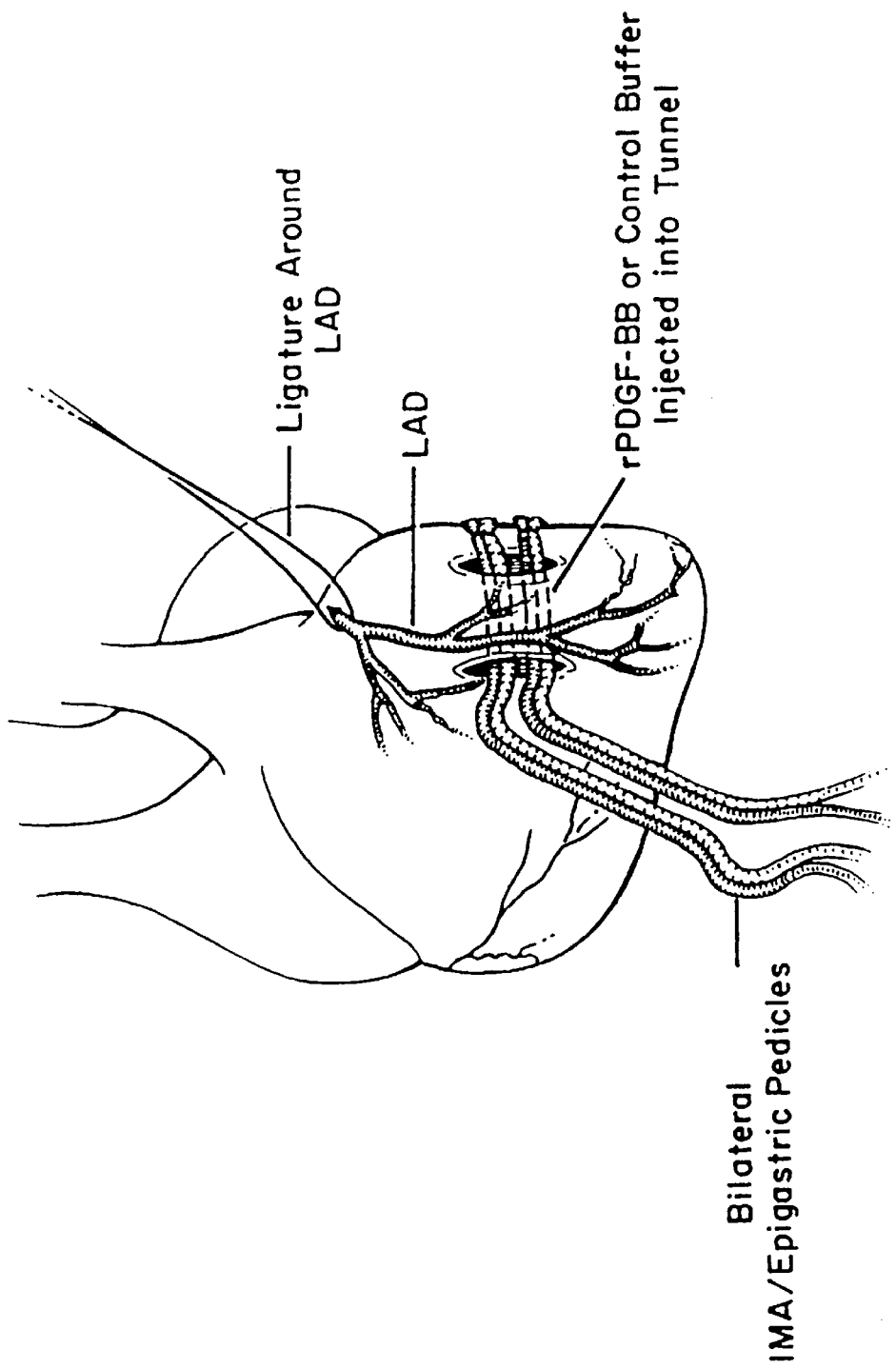
FIG. 8 is a diagram of an experimental model for PDGF-BB-induced extra-cardiac-to-coronary vascular anastomoses.

Under sterile surgical conditions, the superior epigastric/internal mammary vessels were dissected free bilaterally from the upper abdominal and lower chest walls. The vascular bundles were introduced into the chest cavity through a left thoracotomy incision. A tunnel was created through the left ventricular myocardium in close proximity to the mid portion of the left anterior descending coronary artery (LAD). The vascular bundles were placed through the tunnel with the ligated vessel ends close to the surface of the myocardium (FIG. 8). A 0.5 ml volume of solution was injected into the myocardial tissue surrounding the implanted vessels. The solution contained phosphate-buffered saline either with (treated) or without (treated control) 1 mg/ml concentration of the recombinant PDGF-BB of Example 3, with delivery on a blinded and randomized basis. Prior to closing the thoracotomy, a 4-0 ligature was passed around the LAD proximal to the implanted vessels without tying a knot. Untied ends were buried in the subcutaneous tissue of the chest wall for easy retrieval at the second operation. The chest was closed in layers over a small chest tube that was used to evacuate any remaining air in the pleural space.

Two weeks following the first operation, the rabbits were reanesthetized and the ends of the untied ligature retrieved. The LAD was occluded by direct ligature. A total of 28 rabbits were used, 14 in each of the two groups (treated and treated control). An additional 8 rabbits underwent LAD ligation without implantation of vessels or myocardial injection, thus serving as an untreated control group.

Four days after LAD ligation, microangiography was performed by injecting contrast medium through the implanted vessels of the surviving animals. both internal mammary arteries were cannulated with a 30-gauge catheter using an operating microscope for isualization. After briefly flushing the vessels with eparinized saline, 20 ml of a lead oxide/gelatin radiopaque solution were injected. The heart and implanted vessels were removed from the chest, left at 4° C. overnight, and x-rayed using a stationary mammography system at 12 mA, 25 kV for 0.20 seconds to maximize resolution. Rees and Taylor, *Plast. Reconstr. Surg.*, 77, 141–145 (1986).

Histochemical staining using triphenyltetrazolium chloride (TTC) was used to identify regions of infarction. Lie et al., *J. Thorac. Cardiovasc. Surg.*, 69, 599–605 (9175). The left ventricle was transversely sectioned into 3 mm thick slices and the extent of the infarct (unstained tissue) was determined by computerized planimetry and 3-dimensional reconstruction. The slices were then immersion-fixed in buffered formalin, then processed for histological analysis using hematoxyline and eosin stains.

The proportions of surviving animals between groups were compared with the Fisher exact test. The average volume of infarcted zone in surviving animals was compared between groups with Student's t-test.

Only 50% (4 of 8) of the untreated control animals survived acute ligation of the LAD. The ECG manifested large ST-segment elevations indicative of severe myocardial injury. Implantation of the extra-cardiac vessels without PDGF-BB treatment (treated control group) did not alter survival, with 57% (8 of 14) of the treated control group surviving. The ECG of the treated control animals was similar to the untreated control animals, although in 4 of the 8 treated control survivors, the ST elevations reverted to baseline within 10–15 minutes. With PDGF-BB treatment around the implanted vessels (treated group), survival significantly improved to 93% (13 of 14; p<0.05). All survivors in the treated group demonstrated a return to baseline of the ST-segment elevations within 10–15 minutes.

Figure 9:
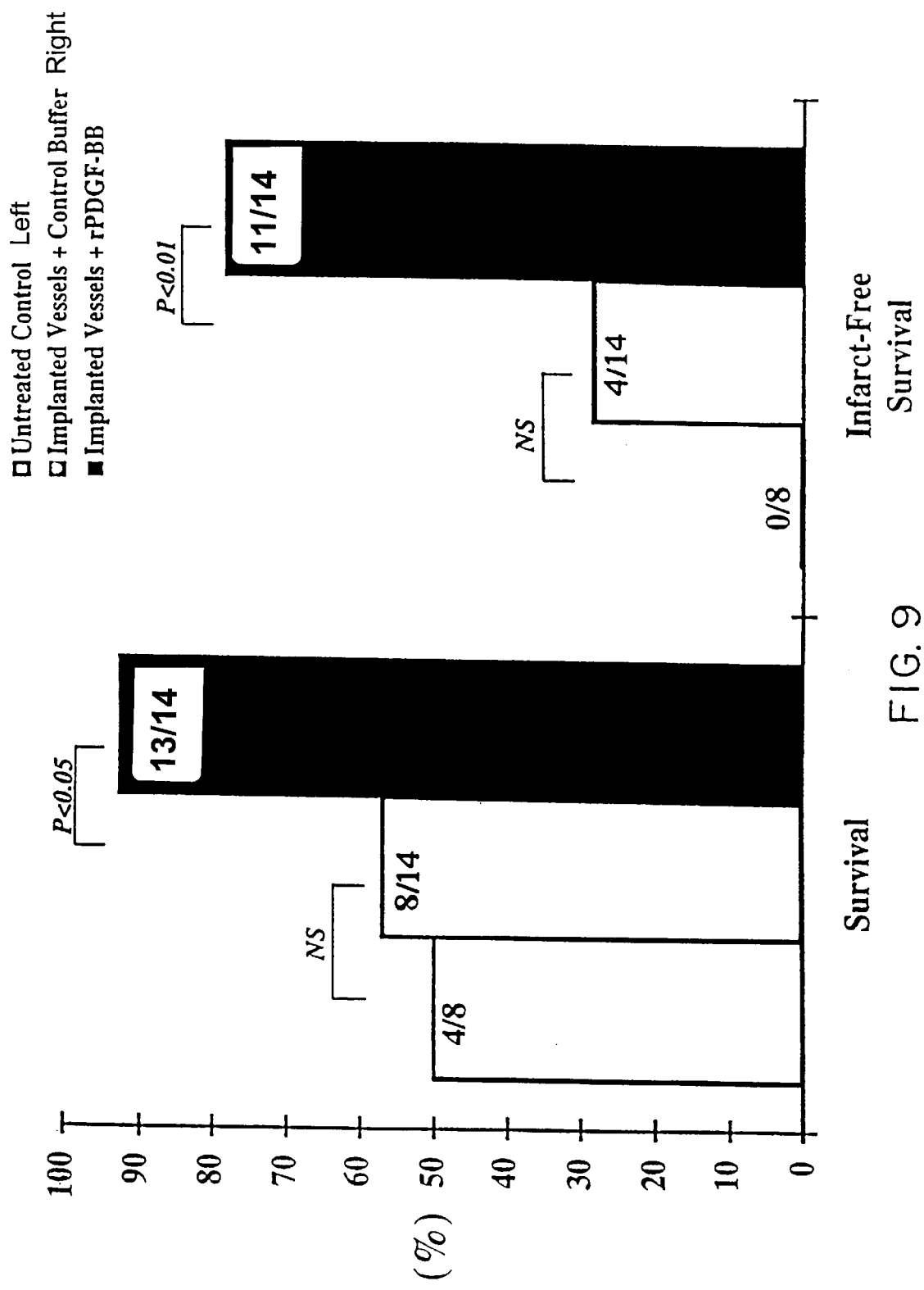
FIG. 9 is a bar graph showing the effect of PDGF-BB treatment on survival and infarct-free survival following acute occlusion of the left anterior descending artery.
Figure 10:
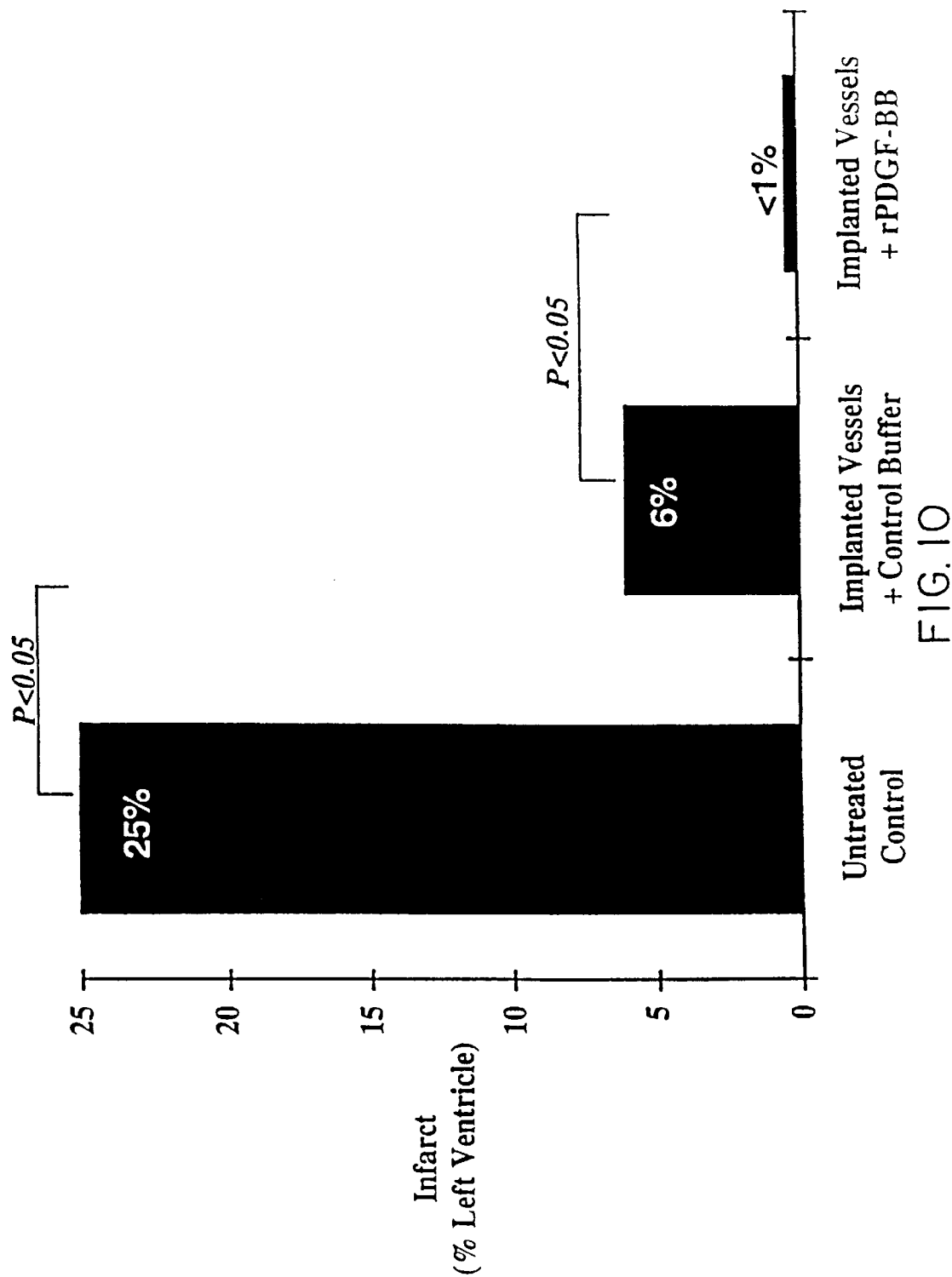
FIG. 10 is a bar graph showing the effect of PDGF-BB treatment on infarct size following acute occlusion of the left anterior descending artery.
Figure 11:
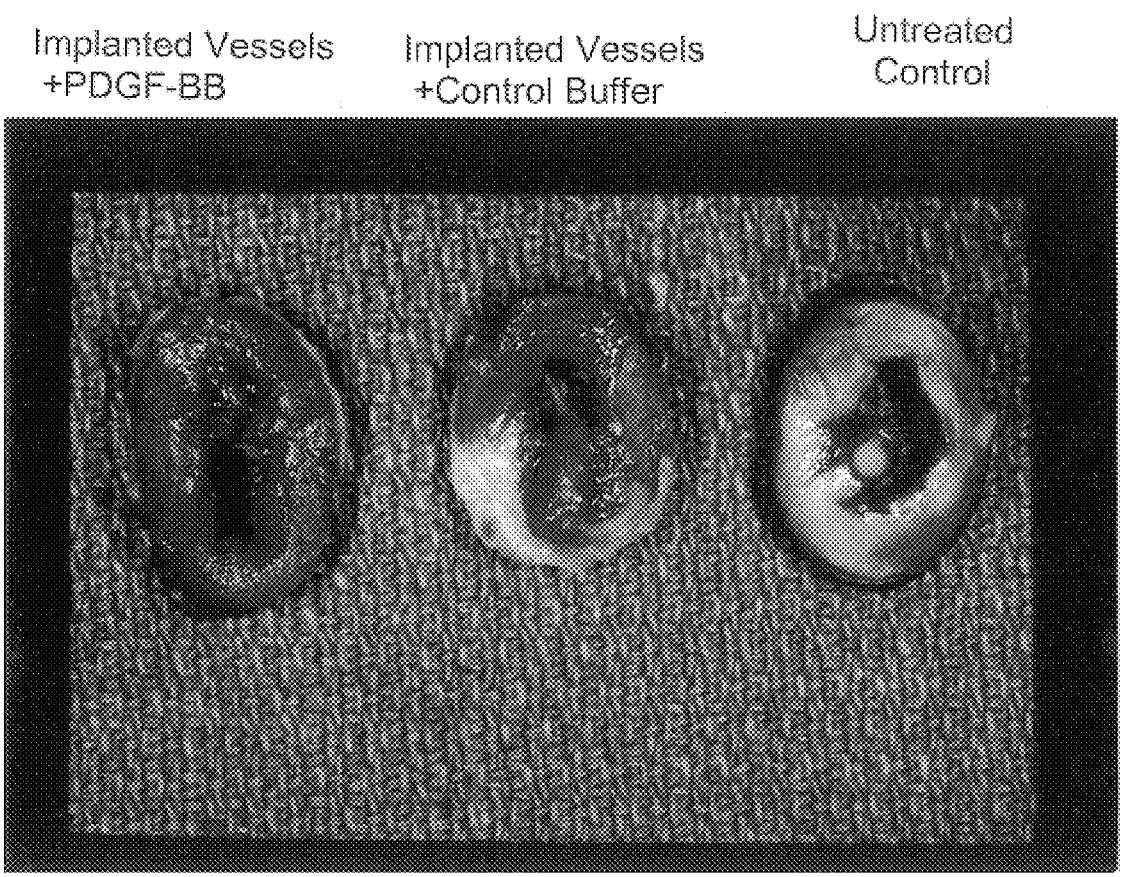
FIG. 11 shows representative gross pathological cross-sections of the left ventrical from each group of rabbits in Example 7.

None of the untreated control animals was free of myocardial infarction, whereas 4 of the 8 surviving animals in the treated control group (implanted vessels without PDGF) were free of infarction (p<0.5). In contrast, 11 of the 13 PDGF-BB treated surviving animals were free of infarction (p<0.01 vs. either control group), as shown in the bar graph of FIG. 9. The average zone of infarction (as a percentage of the entire left ventricle) was significantly smaller in the PDGF-BB injected hearts in comparison to both untreated and vehicle-injected hearts, as shown in the bar graph of FIG. 10. Representative gross pathological cross-sections of the left ventricle from rabbits in each group are shown in FIG. 11, with the unstained (white) area representing the area of infarct.

Figure 12A:
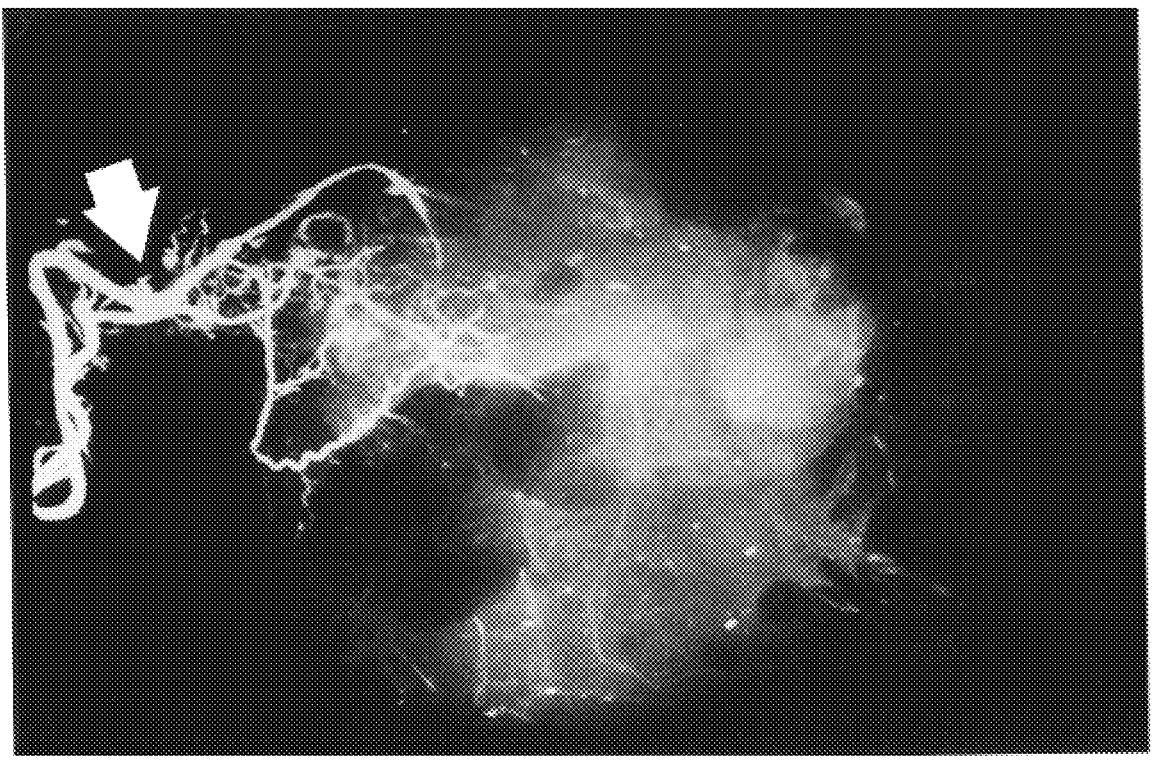
FIG. 12A is a microangiogram of the control group from Example 7.
Figure 12B:
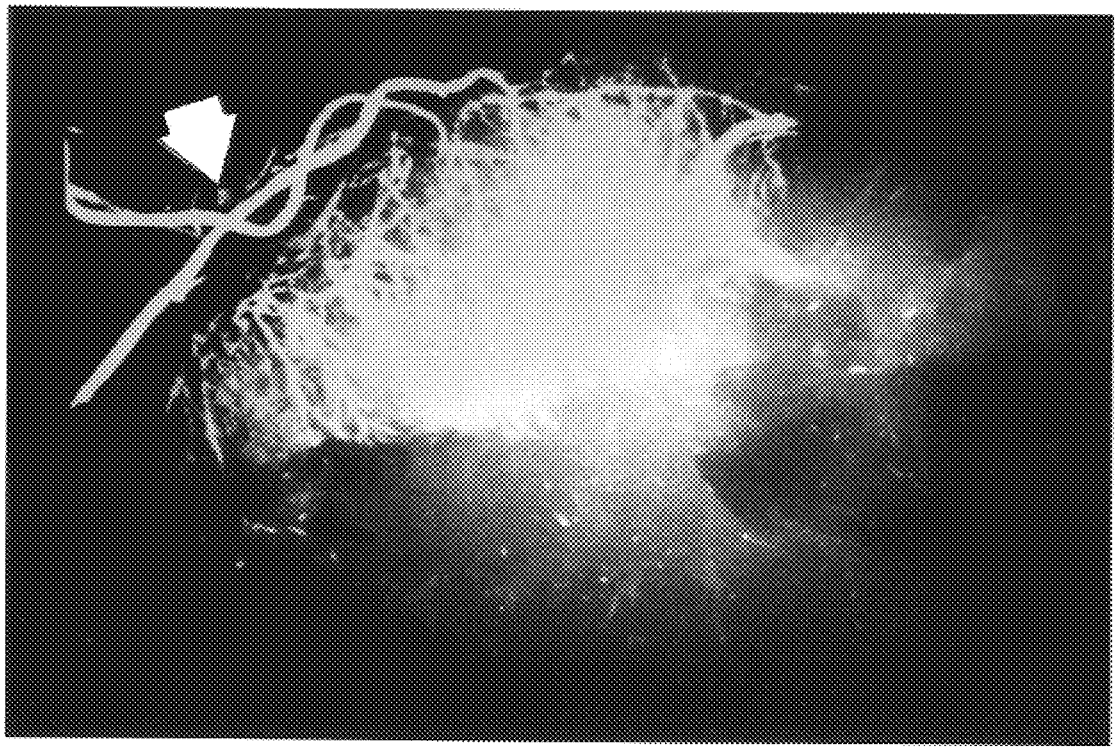
FIG. 12B is a microangiogram of the PDGF-BB-treated group from Example 7.

Microangiography through the implanted vessels of the treated control group revealed patent vessels to the surface of the heart but without filling the coronary circulation (extra-cardiac vascular pedicles designated by the arrow), as shown in FIG. 12A. In contrast, there was extensive filling of the coronary vasculature in the region of the LAD distribution for hearts injected with PDGF-BB (treated group), as shown in FIG. 12B. Histological analysis confirmed the communication between the implanted vessels and the LAD.

---

What is claimed is:

1. A method for anastomosing divided blood vessels in a human or animal subject comprising administering, in or about the area of the divided ends of said blood vessels, an amount of a biologically active growth factor from the platelet-derived growth factor (PDGF) family effective to anastomose said divided blood vessels.

2. A method for anastomosing divided blood vessels in a human or animal subject comprising administering, in or about the area of the divided ends of said blood vessels, an amount of a biologically active platelet-derived growth factor (PDGF) wherein the PDGF is a naturally occurring PDGF or comprises a PDGF-$B_{119}$.

3. The method of claim 2 wherein said PDGF is administered directly to said divided ends of said blood vessels.

4. The method of claim 3 wherein said PDGF is administered endoscopically.

* * * * *

UNITED STATES PATENT AND TRADEMARK OFFICE
CERTIFICATE OF CORRECTION

PATENT NO. : 6,086,866
DATED : July 11, 2000
INVENTOR(S) : Roger Khouri

Page 1 of 1

It is certified that error appears in the above-identified patent and that said Letters Patent is hereby corrected as shown below:

Item [76], Inventors,
Inventors's name is KHOURI

Signed and Sealed this

Twenty-eighth Day of August, 2001

*Attest:*

*Nicholas P. Godici*

NICHOLAS P. GODICI
*Attesting Officer*    *Acting Director of the United States Patent and Trademark Office*